(12) United States Patent
Walter et al.

(10) Patent No.: US 7,355,065 B2
(45) Date of Patent: Apr. 8, 2008

(54) PROCESS FOR THE PREPARATION OF 4,4-DIFLUORO-3-OXOBUTANOIC ACID ESTERS

(75) Inventors: Harald Walter, Basel (CH); Camilla Corsi, Basel (CH); Josef Ehrenfreund, Basel (CH); Clemens Lamberth, Basel (CH); Hans Tobler, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 11/572,053

(22) PCT Filed: Jul. 13, 2005

(86) PCT No.: PCT/EP2005/007635

§ 371 (c)(1),
(2), (4) Date: Jan. 12, 2007

(87) PCT Pub. No.: WO2006/005612

PCT Pub. Date: Jan. 19, 2006

(65) Prior Publication Data

US 2008/0004465 A1    Jan. 3, 2008

(30) Foreign Application Priority Data

Jul. 14, 2004    (GB) ................. 0415764.0

(51) Int. Cl.
*C07C 69/72*    (2006.01)
(52) U.S. Cl. ..................... 560/178
(58) Field of Classification Search ............ None
See application file for complete search history.

(56) References Cited

U.S. PATENT DOCUMENTS 5,498,624 A    3/1996    McLoughlin et al.

FOREIGN PATENT DOCUMENTS

EP    694526 A1    1/1996
WO    0142223    6/2001

OTHER PUBLICATIONS

Jones, R.G., "The Synthesis of Ethyl Ethoxymethyleneoxalacetate and Related Compounds", Journal of the American Chemical Society, 1951, 73(8):3684-3686.
Tomoya Kitazume et al.: "A Microbially-Based Approach for the Synthesis of Chiral Secondary Alcohols Bearing the Difluoromethyl of Chlorodifluoromethyl Group"; Journal Of Fluorine Chemistry, vol. 56, 1992, pp. 271-284, XP002347794; Elsevier Sequoia. Luasanne, CH, p. 273, ethyl 4,4-difluoro-3-oxobutanoate (3a).
McBee E.T. et al.: "The Preparation and Reactions of Fluorine-Containing Acetoacetic Esters", Journal Of The American Chemical Society, American Chemical Society, Washington, DC, US, vol. 1, No. 13, Jul. 5, 1953, pp. 3152-3153, XP000652734, ISSN: 0002-7863, cited in the application p. 3153, Table 1, entry 7.
A. L. Henne et al.: "The Alkaline Condensation of Fluorinated Esters With Esters and Ketones", Journal Of The American Chemical Society, vol. 69, No. 7, 1947, pp. 1819-1820, XP002347795, American Chemical Society, Washington, DC, US, cited in the application, the whole document.
N. D. Priestley: Nonactin Biosynthesis: The Initial Committed Step Is the Condensation of Acetate (Malonate) and Succinate, Journal Of The American Chemical Society, vol. 124, No. 12, 2002, pp. 2894-2902, XP002347796, American Chemical Society, Washington, DC, US p. 2898-9, Benzyl 3-oxobutanoate (15).

*Primary Examiner*—Paul A. Zucker
(74) *Attorney, Agent, or Firm*—Thomas Hamilton

(57) ABSTRACT

The present invention relates to a process for the preparation of a compound of the formula (I), wherein R is $C_{1-12}$ alkyl, by the contact of a compound of the general formula (II), wherein $R_1$ and $R_2$ are each, independently, $C_{1-12}$ alkyl; or $R_1$ and $R_2$ join together with the nitrogen atom to which they are attached to form an alicyclic amine ring containing 4 to 7 carbon atoms or a morpholine ring, with an acetic acid ester of the general formula (III) $CH_3COOR$, wherein R is as defined under formula (I), in the presence of a base.

10 Claims, No Drawings

PROCESS FOR THE PREPARATION OF 4,4-DIFLUORO-3-OXOBUTANOIC ACID ESTERS

This application is a 371 of International Application No. PCT/EP2005/007635 filed Jul. 13, 2005, which claims priority to GB 0415764.0 filed Jul. 14, 2004, the contents of which are incorporated herein by reference.

The present invention relates to a novel process for preparing 4,4-difluoromethyl-3-oxo-butanoic acid esters. These esters are useful for preparing 3-difluoromethyl-4-pyrazole carboxylic acid esters which are important intermediates for the manufacture of pyrazole carboxanilide fungicides.

Various pyrazole carboxanilide fungicides and their preparation are described for example in U.S. Pat. No. 5,498,624 and in WO 01/42223. The preparation of many of these fungicides requires the use of an ester of 3-difluoromethyl-1-methyl-4-pyrazole carboxylic acid. In U.S. Pat. No. 5,498,624 the ethyl ester of this carboxylic acid is prepared by the reaction of methyl hydrazine and ethyl 2-(ethoxymethylene)-4,4-difluoromethyl acetoacetate in ethanol. This latter compound is prepared by the method described in JACS, 73, 3684 (1951), which involves the condensation of ethyl orthoformate and acetic anhydride with ethyl difluoroacetoacetate.

The synthesis of methyl and ethyl difluoroacetoacetates, also known as the methyl and ethyl esters of 4,4-difluoro-3-oxo-butanoic acids, by reacting the corresponding fluorinated esters with acetic acid esters under basic conditions has been known since a long time and described in, for example, JACS, 69, 1819 (1947) and JACS, 75, 3152 (1953). When a weaker base, such as sodium ethylate, is used, the yields of this reaction are not satisfactory for commercial large-scale production processes. For example, the yield when using sodium ethylate is only 35%, as described in JACS, 69, 1819 (1947). It is known in the literature, that yields of those type of reactions can be increased by using a much stronger base, such as sodium hydride, see for example in JACS, 75, 3152 (1953), there it is reported that the yield can be increased up to 75-85% when using sodium hydride as a base. However, it is undesirable to use sodium hydride for commercial productions, because it is dangerous to work with on a large scale and presents the hazard of large amounts of explosive hydrogen gas.

An alternative synthesis route is described in EP-A-694526. Here, methyl and ethyl polyfluoroacetoacetates are prepared by the reaction of a polyfluoro carboxylic acid chloride or anhydride with a carboxylic acid chloride in the presence of a tertiary amine base, such as pyridine. The reaction is completed by addition of an alcohol, such as methanol or ethanol. This synthesis route can be used conveniently for the production of trifluoroacetoacetates with average yields of 52%, but it is unsatisfactory for the production of difluoroacetoacetates. The difluoroacetic acid chlorides or anhydrides are not sufficiently stable under these conditions. For example, EP-A-694526 describes the synthesis of methyl 2-difluoroacetylbutanoate by the reaction of difluoroacetic anhydride with butyryl chloride. The yield for this reaction is only 25% of theory. Such low yields are not acceptable for commercial production of chemical compounds.

The aim of the present invention is therefore to provide a novel general process for the preparation of esters of 4,4-difluoro-3-oxo-butanoic acid, by means of which it is possible to prepare such compounds in high yields and good quality, by a simple reaction procedure and with low expenditure, without the above-mentioned disadvantages of the known processes.

Thus, according to the present invention there is provided a process for the preparation of a compound of the formula (I)

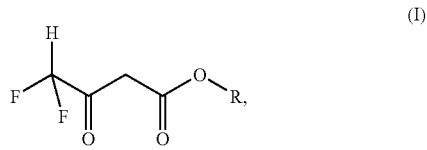

wherein R is $C_{1-12}$ alkyl, which comprises contacting a compound of the general formula (II)

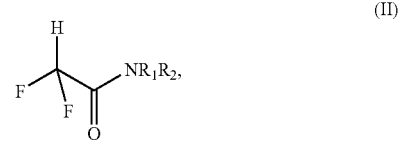

wherein $R_1$ and $R_2$ are each, independently, $C_{1-12}$ alkyl; or $R_1$ and $R_2$ join together with the nitrogen atom to which they are attached to form an alicyclic amine ring containing 4 to 7 carbon atoms or a morpholine ring;

with an acetic acid ester of the general formula (III)

wherein R has the meaning given above, in the presence of a base.

R is a branched or unbranched alkyl group containing from 1 to 12 carbon atoms and is, for example, methyl, ethyl, n-propyl, n-butyl, iso-propyl, sec-butyl, iso-butyl, tert-butyl, n-pentyl, n-hexyl, n-heptyl, n-octyl, n-nonyl, n-decyl, n-undecyl or n-dodecyl. Conveniently it is methyl or ethyl.

$R_1$ and $R_2$ are branched or unbranched alkyl groups containing from 1 to 12 carbon atoms and are, for example, methyl, ethyl, n-propyl, n-butyl, iso-propyl, sec-butyl, iso-butyl, tert-butyl, n-pentyl, n-hexyl, n-heptyl, n-octyl, n-nonyl, n-decyl, n-undecyl or n-dodecyl. They may be the same or different. Typically they are both methyl or both ethyl.

Alternatively, $R_1$ and $R_2$ join together with the nitrogen atom to which they are attached to form an alicyclic amine ring containing 4 to 7 carbon atoms or a morpholine ring. Examples of such alicyclic amine rings are pyrrolidine and piperidine. When $R_1$ and $R_2$ join with the nitrogen atom to which they are attached to form a ring, the ring is conveniently a pyrrolidine or morpholine ring.

R is preferably $C_{1-6}$ alkyl, more preferably methyl or ethyl.

In a preferred embodiment $R_1$ and $R_2$ are each, independently, $C_{1-8}$ alkyl; or $R_1$ and $R_2$ join together with the nitrogen atom to which they are attached to form an alicyclic amine ring containing 4 to 7 carbon atoms or a morpholine ring.

In one further preferred embodiment $R_1$ and $R_2$ are each, independently, $C_{1-8}$ alkyl, preferably both methyl or both ethyl.

In another further preferred embodiment $R_1$ and $R_2$ join together with the nitrogen atom to which they are attached to form an alicyclic amine ring containing 4 to 7 carbon atoms or a morpholine ring. In a particular preferred embodiment $R_1$ and $R_2$ join with the nitrogen atom to which they are attached to form a pyrrolidine or morpholine ring.

The process is conveniently carried out in a solvent, which may be an excess of the acetic acid ester (III) or a different solvent or a mixture of both. If it is a mixture of both, the acetic acid ester acts as a cosolvent. Suitable 'different' solvents include $C_1$-$C_8$ alcohols; aromatic or halogenated aromatic solvents such as toluene, xylene and chlorobenzene; and ethers such as tetrahydrofuran, dioxane and tert-butylmethylether.

When the acetic acid ester (III) is used as the solvent or as a cosolvent, it is employed in a large excess, typically in excess of 10 molar equivalents (preferably 10-30 molar equivalents) of the compound of formula (II).

Any suitable base may be used in the process of the invention, but it will usually be an alkoxide base, typically an alkali metal alkoxide base, such as an alkali metal $C_{1-4}$ alkoxide base. Examples are sodium methoxide, sodium ethoxide and sodium tert-butoxide. Preferably the base is sodium methoxide or sodium ethoxide. In order to optimise the yield of product (I), the amount of base used is from 1 to 4 molar equivalents of the compound of formula (II).

The process is conveniently carried out at a temperature in the range of 15° C. to 80° C., for example, from 45° C. to 80° C., and typically from 50° C. to 70° C. Thus, when an ethanolic solution of an alkoxide base is used with ethyl acetate as a cosolvent, the process may be carried out from anywhere between ambient temperature and the reflux temperature of the combined solvents.

The time the process takes will depend upon, inter alia, the scale of the preparation and the temperature at which it is carried out. For example, it may take from half an hour to 24 hours. Typically a laboratory preparation on a less than a molar scale may take from 1 to 6 hours.

Conveniently, the process is carried out by dissolving a compound of formula (II) in an acetic acid ester of formula (III), optionally in the presence of another solvent. An alcoholic or other solvent solution of the base is then added with stirring at ambient or elevated temperatures. The mixture is then heated to 50 to 70° C. until the reaction is complete. After cooling, the mixture is poured into an acidified ice-water mix, and extracted with a suitable solvent such as diethyl ether or ethyl acetate. The product may then be recovered from the organic extract by washing with brine, evaporating the solvent and, if necessary, purifying the residual product by distillation under reduced pressure.

The invention also embraces embodiments wherein mixtures of 4,4-difluoromethyl-3-oxo-butanoic acid esters are produced. For example, the use of ethylacetate as ester and sodium methoxide as base, leads to a mixture of 4,4-difluoromethyl-3-oxo-butanoic acid ethyl ester and 4,4-difluoromethyl-3-oxo-butanoic acid methyl ester.

Compounds of the general formula (II)

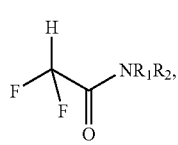

wherein $R_1$ and $R_2$ are each, independently, $C_{1-12}$ alkyl; or $R_1$ and $R_2$ join together with the nitrogen atom to which they are attached to form an alicyclic amine ring containing 4 to 7 carbon atoms or a morpholine ring; may be prepared by the method described in JP-A-06228043. This involves the fluorination of an N,N-disubstituted dichloroacetic acid amide, the N,N-disubstituted dichloroacetic acid amide being prepared by the reaction of dichloroacetyl chloride with a secondary amine. The methodology is summarised in the following schematic diagram.

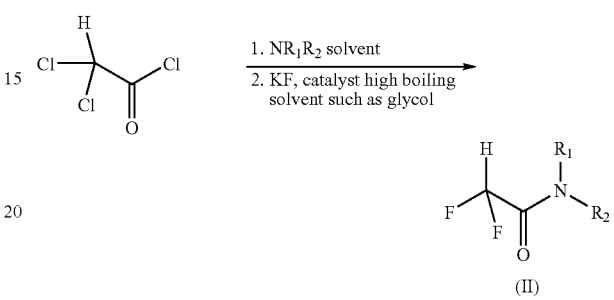

Acetic acid esters of the general formula (III)

$$CH_3COOR \qquad (III),$$

wherein R is $C_{1-12}$ alkyl, are known and commercially available.

The following non-limiting examples illustrate the invention in more detail.

EXAMPLE 1

Preparation of 2,2-dichloro-N,N-dimethyl acetamide

In a sulfonation flask, a solution consisting of dichloroacetyl chloride (110 g; 0.75 mol) and toluene (100 ml) was slowly added, over a period of 1 hour, to a solution of dimethylamine (68 g; 1.5 mol) and toluene (1.21) initially at 0° C., maintaining the temperature of the reaction mixture at below 10° C. throughout. The reaction mixture was stirred for a further 30 minutes at 0-5° C. and was then gradually diluted by toluene (11). The organic phase was washed consecutively with water (1×500 ml), hydrochloric acid (5% solution; 2×500 ml), water (1×500 ml), a saturated sodium bicarbonate solution (2×500 ml) and finally brine (1×500 ml) and was then dried over sodium sulfate. Evaporation furnished a residue, which was distilled at high vacuum to yield 2,2-dichloro-N,N-dimethylacetamide as a colourless oil.

Yield 78.6 g (67.2%); b.pt. 65-67° C. at 0.3 mbar.

EXAMPLE 2

Preparation of 2,2-difluoro-N,N-dimethylacetamide

In a sulfonation flask, a mixture of 2,2-dichloro-N,N-dimethylacetamide (23.4 g; 0.15 mol), spray dried potassium fluoride (26.1 g; 0.45 mol) and diethylene glycol (150 ml) was heated to 183° C. at 160 mbar in a distillation apparatus fitted with a VIGREUX column (10 cm). Under these conditions, the desired product was distilled as a colourless oil over 1 hour.

Yield 12.3 g (66.7%); b.pt. 105-108° C. at 160 mbar.

EXAMPLE 3

Preparation of 4.4-difluoro-3-oxo-butanoic acid ethyl ester

In a sulfonation flask, N,N-diethyl-2,2-difluoroacetamide (1.51 g; 10 mmol) was dissolved in ethyl acetate (20 ml) before ethanolic sodium ethoxide (15 ml of a 21% solution; 40.2 mmol) was added dropwise. The resulting mixture was stirred at 60° C. for 6 hours. After cooling, the mixture was poured into ice-water (20 ml), acidified with hydrochloric acid (10%) and extracted with ethyl acetate. The organic phase was washed with brine, dried over sodium sulfate and evaporated in a water jet vacuum. The residue was purified by distillation under reduced pressure to give the desired 4,4-difluoro-3-oxo-butanoic acid ethyl ester in the form of a colourless oil.

Yield 1.09 g (66%); b.pt. 50-53° C. at 18 mbar.

EXAMPLE 4

Alternative Preparation of 4,4-difluoro-3-oxo-butanoic acid ethyl ester.

In a sulfonation flask, sodium ethoxide in ethanol (79 ml of a 21% solution; 0.243 mol) was added dropwise to a solution of 2,2-difluoro-N,N-dimethyl-acetamide (27.2 g; 0.22 mol) in ethylacetate (460 ml). The reaction mixture was heated at reflux temperature for 1 hour and the disappearance of the starting material was monitored by GC. The reaction mixture was then poured in to ice-water (800 ml), acidified with hydrochloric acid (10%) and then extracted twice with ethylacetate (2×200 ml). After separation, the organic layer was washed with brine (200 ml), dried over sodium sulfate and concentrated under reduced pressure (40° C. at 100 mbar).

Ethyl 4,4-difluoro-3-oxo-butanoic acid ethyl ester was obtained as a dark oil (34.8 g; 72%) containing some ethanol as an impurity; the purity of the product was established as ca.75% by the use of GC.

EXAMPLE 5

Preparation of a Mixture of 4,4-difluoro-3-oxo-butanoic acid ethyl ester and 4,4-difluoro-3-oxo-butanoic acid methyl ester In a sulfonation flask, sodium methoxide in methanol (165.7 g of a 30% solution; 0.92 mol) was added dropwise to a solution of 2,2-difluoro-N,N-dimethyl-acetamide (98.5 g; 0.8 mol) in ethylacetate (1570 ml) at 60° C. The reaction mixture was heated at reflux temperature for 3 hours and the disappearance of the starting material was monitored by GC. The reaction mixture was then poured into cold hydrochloric acid ice-water (3%, 1100 ml), and then extracted twice with ethylacetate (640 ml). The combined organic layers were concentrated under reduced pressure (40° C. at 150 mbar).

A mixture of 4,4-difluoro-3-oxo-butanoic acid ethyl ester and 4,4-difluoro-3-oxo-butanoic acid methyl ester was obtained as a dark oil containing 81% ethyl ester and 19% methyl ester (121.8 g; 90% combined yield for both esters) containing some ethylacetate as an impurity.

According to the present invention it is possible to prepare compounds of formula I in good yields and with little effort.

A special advantage of the process according to the invention is that the starting compounds of formula II are readily obtainable and easy to handle.

A further special advantage of the process according to the invention is that the starting compounds of formula III are commercially available, inexpensible and easy to handle.

The invention claimed is:

1. A process for the preparation of a compound of the formula (I)

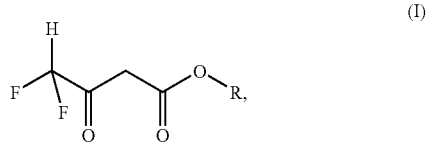

wherein R is $C_{1-12}$ alkyl,
which comprises contacting a compound of the general formula (II)

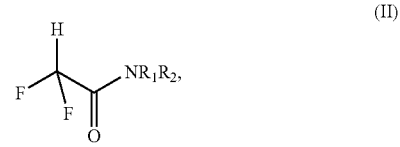

wherein $R_1$ and $R_2$ are each, independently, $C_{1-12}$ alkyl; or $R_1$ and $R_2$ join together with the nitrogen atom to which they are attached to form an alicyclic amine ring containing 4 to 7 carbon atoms or a morpholine ring,
with an acetic acid ester of the general formula (III)

$$CH_3COOR \qquad (III),$$

wherein R is as defined under formula I,
in the presence of a base.

2. A process according to claim 1 wherein R is methyl or ethyl.

3. A process according to claim 1 wherein $R_1$ and $R_2$ are both methyl or both ethyl.

4. A process according to claim 1 wherein $R_1$ and $R_2$ join together with the nitrogen atom to which they are attached to form a pyrrolidine or morpholine ring.

5. A process according to claim 1 which is carried out in a solvent, the solvent being an excess of the acetic acid ester (III) or a different solvent or a mixture of both.

6. A process according to claim 1 wherein the different solvent is a $C_1$-$C_9$ alcohol, an aromatic or halogenated aromatic solvent; or an ether.

7. A process according to claim 1 wherein the amount of acetic acid ester (III) used is in excess of 10 molar equivalents of the compound of formula (II).

8. A process according to claim 1 wherein the base is an alkali metal alkoxide.

9. A process according to claim 8 wherein the alkali metal alkoxide is sodium methoxide or sodium ethoxide.

10. A process according to claim 1 which is carried out at a temperature in the range of 15° C. to 80° C.

* * * * *